United States Patent [19]

Bertele et al.

[11] 3,935,275

[45] Jan. 27, 1976

[54] PROCESS FOR PREPARATION OF TERPENE FLAVORANTS AND NOVEL INTERMEDIATES THEREFOR

[75] Inventors: Erhard Bertele, Dubendorf; Peter Schudel, Grut near Wetzikon, both of Switzerland

[73] Assignee: Givaudan Corporation, Clifton, N.J.

[22] Filed: Jan. 25, 1974

[21] Appl. No.: 436,754

Related U.S. Application Data

[62] Division of Ser. No. 742,178, July 3, 1968, Pat. No. 3,872,172.

[52] U.S. Cl. ........................................ 260/603 HF
[51] Int. Cl.² ........................................ C07C 45/16
[58] Field of Search ............................ 260/603 HF

[56] References Cited
UNITED STATES PATENTS
3,637,721   1/1972   Pappas et al. .................... 260/601 R FOREIGN PATENTS OR APPLICATIONS
813,539   5/1959   United Kingdom ............. 260/601 R OTHER PUBLICATIONS
Sutherland, M. D., Chemical Abstracts, Vol. 74, p. 2688, 1952.
Bestmann, H. J., Bull. Soc. Chim., 1971, pp. 1619–1631.
Cram et al., Organic Chemistry, 2nd Edit., 1964, pp. 345, 416–417.

Primary Examiner—James O. Thomas, Jr.
Assistant Examiner—R. H. Liles
Attorney, Agent, or Firm—Thomas Cifelli, Jr.

[57] ABSTRACT

A process for preparing compounds of the type of sinensal, which is suitable as a flavor-imparting agent of orange aroma, and novel intermediates including those having the general formula:

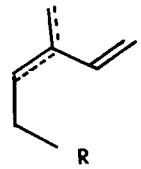

wherein R signifies a CH$_2$OH, CHO or COOH group and the broken lines present a double bond emanating from C-atom 4, are disclosed.

3 Claims, No Drawings

PROCESS FOR PREPARATION OF TERPENE FLAVORANTS AND NOVEL INTERMEDIATES THEREFOR

This is a division of application Ser. No. 742,178 filed July 3, 1968, now U.S. Pat. No. 3,872,172.

SUMMARY OF THE INVENTION

This invention provides a commercially-feasible process for making unlimited quantities of compounds of the type of the previously-rare sinensal, thereby permitting the widespread use of this product as a flavorant to impart an orange flavor and aroma to food products such as orange drinks.

Novel intermediates, some of which also possess flavorant properties, are also the subject of this invention.

DETAILED DESCRIPTION OF THE INVENTION

The process in accordance with this invention for the manufacture of compounds of formula I is characterized in that a compound of the formula

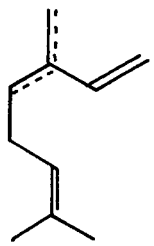

II is ozonized and the ozonization product which is obtained is decomposed to give a compound of general formula I.

Cis or trans ocimene or, preferably, myrcene can be used as the starting material of formula II.

If in formulae I and II the double bond which is conjugated with the terminal double bond lies with the chain (as is the case in ocimene), formulae I and II are meant to represent not only the cis but also the trans isomers.

The ozonization of the trienes II surprisingly proceeds with high selectivity, since the ozonide linkage is practically exclusively effected at the isolated double bond, and so the conjugated double bonds practically do not enter into reaction with the ozone.

The ozonization can be undertaken according to methods known per se, by bringing ozone-containing gas into contact with the triene which is to be ozonized, conveniently by introduction of the gas into a preferably dilute solution of the triene. Presently preferred solvents are those which are inert to ozone, or at least display greater stability than the substance which is to be ozonized; for example, alkanes such as hexane, petroleum ether, cyclohexane; benzene and its derivatives; halogenated hydrocarbons such as carbon tetrachloride, chloroform, methylene chloride, methyl chloride, ethyl chloride, ethyl bromide; esters such as formic acid or acetic acid esters (ethyl acetate); ketones such as acetone or methyl ethyl ketone; ethers such as dimethyl ether, diethyl ether, tetrahydrofuran; acid anhydrides such as acetic anhydride; acid amides such as formamide, dimethylformamide; nitromethane etc. Among other solvents which may be used are those which enter into reaction with ozonide which is primarily formed: for example, carboxylic acids (for example, formic acid, acetic acid, propionic acid); alcohols such as methanol, ethanol, propanol; water in admixture with acetone. Best suited are solvents which are able to hold the ozonization products in solution. Furthermore, low-boiling solvents are to be preferred, since these are usually readily separable from the reaction products. For the ozonization of myrcene and ocimene, particularly suitable solvents are, for example: methyl chloride, chloroform, carbon tetrachloride, benzene, acetone, ethyl acetate, methanol.

The concentration of the solution which is to be ozonized can vary within wide limits. In general, dilute solutions give better yields. On practical grounds, 5–20% solutions will usually be used.

Conveniently, not more than about 1 mol equivalent of ozone is allowed to act on the triene II, in order to avoid an oxidation of the reaction products. Normally, an oxygen stream with an ozone content of about 2–10% is used. However, more dilute and more concentrated ozone mixtures also may be employed. If desired, oxygenfree ozone (as the gas or as a solution) may also be used.

The ozonization is advantageously carried out at temperatures below room temperature, conveniently at temperatures below 0°C. Particularly good yields are obtained at temperatures within the range of about −50° to −90°C.

The cleavage of the ozonization products which are primarily obtained to the compounds of general formula I can be undertaken according to methods which are known per se.

The alcohols of the formula

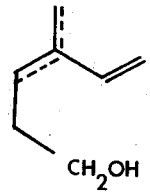

Ia may be obtained by treating the ozonization product which is formed with a powerful reducing agent, of the type known to be suitable to reduce ozonides to alcohols, such as a complex metal hydride (e.g. lithium aluminum hydride or sodium borohydride), hydrogen catalytically activated by noble-or transition metals (e.g. palladium, platinum) or complexes of such metals (as for example tris-triphenylphosphine-rhodiumchloride).

The aldehydes of the formula

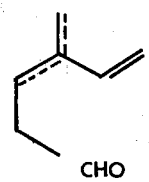

Ib can be obtained from the ozonization products by treatment with a mild reducing agent (of the type known to be suitable to reduce ozonides to aldehydes); for example, an iodide (e.g. sodium or potassium iodide), sulphite, bisulphite (e.g. sodium bisulphite), with formaldehyde, sulphur dioxide, pyridine, hydrazine hydrate, a sulphide (e.g. dimethyl sulphide), hydroquinone, zinc or magnesium in acidic solution, Raney-nickel, phosphorus (III)-compounds (.e.g. phosphines such as triphenylphosphine, tri-loweralkyl-phosphites such as trimethylphosphite), hydrogen [catalytically activated by noble-or transitionmetals or complexes thereof (examples of such systems are pt/H$_2$, Pd/C/H$_2$.)]

The carboxylic acids of the formula

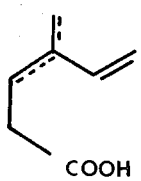

COOH        Ic (i.e. 4-methylene-5-hexenoic acid or 4-methyl-3,5-hexadienoic acid) may be obtained from the primary products of the ozonization by treatment with an oxidizing agent, for example, potassium permanganate, hydrogen peroxide, peracids, chromic acid, oxygen, (catalyzed by manganese or silver salts), silver oxide, peracids (e.g. perbenzoic acid, peracetic acid), etc. Using aluminum hydrides (such as, for example, lithium aluminum hydride), the acids Ic can be reduced directly or, if desired, in the form of their esters, to the corresponding alcohols in a known manner. Likewise, the acids Ic may be converted via the acid chlorides into the amides (e.g. the corresponding N-methyl anilides or N,N-dimethyl amides) which, as is known, can be transformed into the corresponding aldehydes of formula Ib under the influence of aluminum hydrides (such as, for example, of diisobutyl aluminum hydride or lithium diethoxy aluminum hydride). The esters derived from the acids Ic may also be directly converted into the aldehydes of formula Ib at lower temperatures.

The alcohols, aldehydes or carboxylic acids of formulae Ia, Ib or Ic which are obtained by ozonization of the trienes II and by subsequent reductive or oxidative cleavage of the ozonization products, as well as the triene acetals (IV-1 and IV-2) and triene aldehydes (V-1 and V-2) are new compounds which may be used as intermediate products for the manufacture of compounds with orange aroma, especially for the manufacture of the β-sinensal occurring in orange oil (Citrus sinensis) (trans β-sinensal: 2,6-dimethyl10-methylene-2t,6t,11-dodecatrienal), of isomers thereof (cis β-sinensal, cis and trans α-sinensal), as well as of analogues such as, for example, the corresponding alcohols or acid esters which are likewise distinguished by particular aromas (citrus fruit flavours), on the basis of which the compounds can be used for the aromatization, for example, of drinks.

β-sinensal and its isomers (VII), as well as the corresponding alcohol and acid ester analogues, XII and XI, respectively, may be used to impart orange flavor in drinks by incorporation therein in very small amounts, e.g. from ½ to 5 parts per million. These flavorants may be used in conventional manner, for example, in the manner in which the known flavorant, aldehyde C-10, is used.

The aldehyde Ib-1 obtainable from myrcene, or the corresponding alcohol Ia-1, may be converted into cis and trans β-sinensal in accordance with the following schemes:

Scheme A

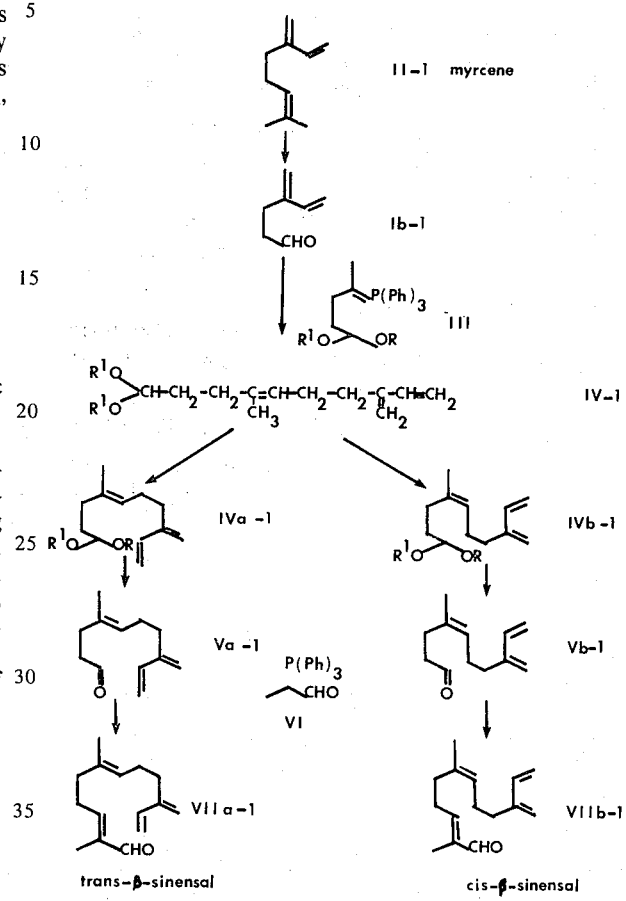

Scheme B

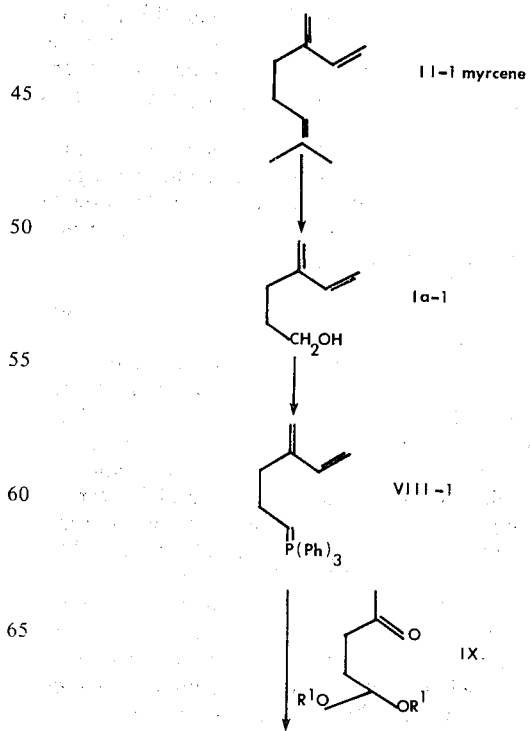

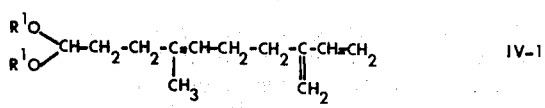

Scheme C

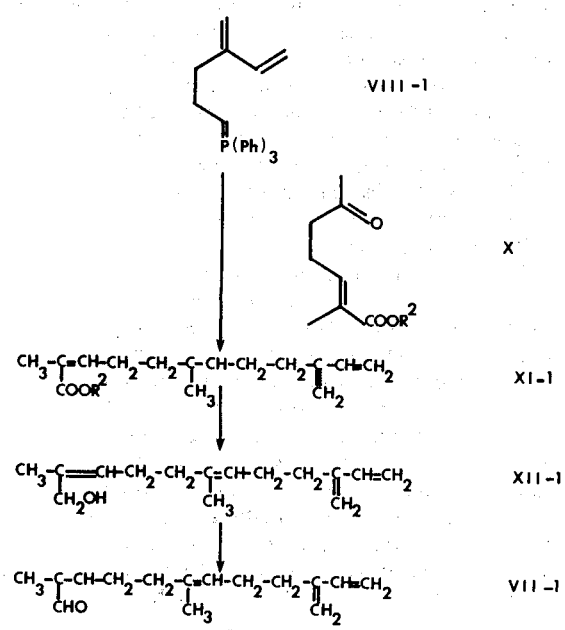

Scheme D

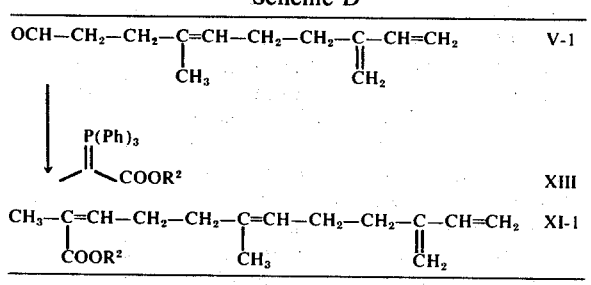

conveniently proceeds in such a way that the carbonyl component is added to a freshly prepared solution or suspension of the phosphorane.

Thereupon, [if desired after separation of the mixture of the cis and trans isomers (e.g. by means of preparative gas chromatography)] the triene acetal IV-1 or the isomer triene acetal IV-2 obtained from ocimene

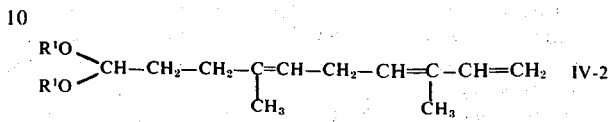

wherein $R^1$ has the same meaning as above, is hydrolysed to the corresponding triene aldehyde of the formula

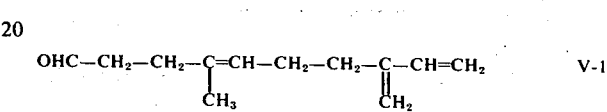

(including the trans isomer Va-1 and the cis isomer Vb-1) or to the triene aldehyde of formula

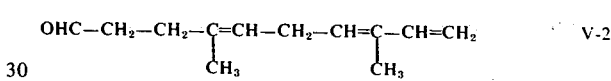

The hydrolysis of the acetals IV-1 and IV-2 to the aldehydes V-1 and V-2 can be brought about according to the usual methods of acetal saponification.

Finally, the triene aldehyde V-1 or V-2 is reacted, again according to Wittig, to give the tetraene aldehyde of the general formula VII-1 or VII-2:

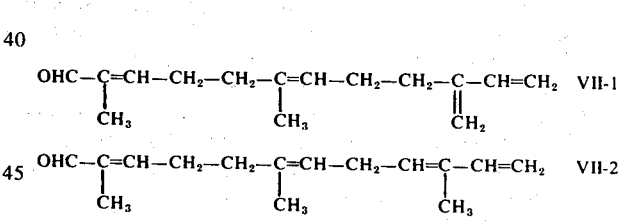

Scheme A: Myrcene (II-1) is converted into the aldehyde Ib-1 (4-methylene-5-hexen-1-al) by ozonisation and subsequent mild reductive cleavage of the ozonisation product. The aldehyde thus obtained is reacted with a phosphorane of general formula III [wherein Ph represents a phenyl group and each $R^1$ signifies a lower alkyl group which can also be linked with each other to form a lower alkylene group (e.g. ethylene)] in a Wittig reaction to give a triene acetal of general formula IV-1. Formula IV-1 includes the trans isomer IVa-1 and the cis isomer IVb-1.

The manufacture of the phosphorane III (as also of the phosphoranes additionally mentioned hereinafter) and the reaction with the carbonyl component Ib-1 can be effected according to the methods of the Wittig reaction which are known per se (see, for example, Angewandte Chemie 71 (1959), 260). In doing so, one by reaction with a phosphorane VI. Formula VII-1 includes the trans isomer VIIa-1 (natural β-sinensal) and the cis isomer VIIb-1. Scheme B: Myrcene (II-1) is converted by ozonisation and subsequent energetic reductive cleavage of the ozonisation product into the alcohol Ia-1 (4-methylene-5-hexen-1-ol). After transformation into the phosphorane VIII-1, this is reacted with the ketone acetal IX in a Wittig reaction to give the triene acetal IV-1 which, as shown in scheme A, can then be worked up to give β-sinensal. By using ocimene as starting material the isomeric triene acetal IV-2 can be obtained similarly.

The transformation of the alcohol Ia-1 into the phosphorane VIII-1 can, for example, be undertaken in such a way that the alcoholic hydroxyl group is exchanged for an iodine atom and the 6-iodo-3-methylene-1-hexene obtained is reacted with triphenyl-phosphine to give the corresponding phosphonium iodide which, after treatment with a strong base such as butyllithium, can then proceed to the reaction with the ketone acetal IX.

Scheme C: The phosphorane VIII-1 which is obtainable in accordance with scheme 3 is reacted according to Wittig with the ketone ester of general formula X (wherein $R^2$ signifies a lower alkyl group) to give the tetraene ester XI-1, this ester is reduced to the corresponding tetraene alcohol XII-1 according to methods known per se (e.g. with lithium aluminium hydride), and the alcohol obtained is oxidised to the corresponding tetraene aldehyde VII-1 ($\beta$-sinensal) according to methods known per se (e.g. with manganese dioxide).

Scheme D: The triene aldehyde V-1 obtained according to Scheme A and B is reacted according to Wittig with the phosphorane XIII (wherein $R^2$ is a lower alkyl group) to give the tetraene ester XI-1 and this is worked up according to Scheme C to give the tetraene aldehyde VII-1.

In an analogous manner the isomeric triene aldehyde V-2 can be converted to the tetraene ester XI-2

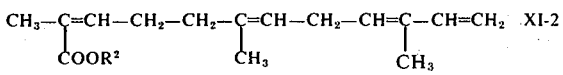

and this worked up via the tetraene alcohol XII-2

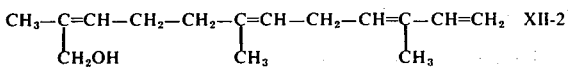

to the tetraene aldehyde VII-2.

The following Examples illustrate the invention, all temperatures being given in degrees centigrade.

EXAMPLE 1

73.5 mmol of ozone are introduced within approximately 3 hours into a solution, cooled to −80°, of 10 g (73.5 mmol) of myrcene in 50 ml of methanol. The still cold solution is then briefly flushed with nitrogen and treated with 6.8 g (110 mmol) of dimethyl sulphide. The cooling-bath is thereupon removed and the reaction mixture allowed to warm up. After approximately 1.5 hours, the mixture is concentrated to approximately one-third of the volume by means of a rotary evaporator (bath-temperature maximum 30°). The residue is taken up in ether and the solution thoroughly shaken twice with water. The solution is dried over sodium sulphate, freed from ether and the residue is distilled at water-jet vacuum. There are obtained 6 g (74% theoretical) of 4-methylene-5-hexen-1-al, boiling point 50°–55°/11 mm, IR-bands at 2,700, 1,750, 1,600, 905 cm$^{-1}$.

EXAMPLE 2

1.51 g (3.0 mmol) of finely powdered (4-ethylenedioxybutyl)-triphenyl-phosphonium iodide are suspended in 10 ml of tetrahydrofuran and treated dropwise with a solution of 4.5 mmol of butyl-lithium in hexane. The solution turns red as the phosphonium iodide goes into solution as (4-ethylenedioxybutylidene)-triphenyl-phosphorane. After approximately 10 minutes, 0.25 ml (4.5 mmol) of methyl iodide are added to this solution, which thereby becomes lighter, and the (4-ethylenedioxy-1-methylbutyl)-triphenyl-phosphonium iodide which is formed partially precipitates as an oil. After 10 minutes, 3.0 mmol of butyl-lithium in hexane are added dropwise and the solution thereby again becomes dark red.

After 10 minutes there are added 330 mg (3.0 mmol) of 4-methylene-5-hexenal (Ib-1) dissolved in 1 ml of tetrahydrofuran to the solution containing the phosphorane III ($R^1+R^1$=ethylene). The solution subsequently partially decolourises and after 30 minutes, 100 mg of sublimed potassium tertbutylate are added. The mixture is stirred for a further 1.5 hours, then taken up in pentane and the insoluble portion which separates out is decanted off. The pentane extract is subsequently washed with water until neutral and dried over sodium sulphate. After removal of the solvent, the residue is distilled. There are thus obtained 421 mg (63%) of a cis-trans isomer mixture of the triene acetal IV-1 ($R^1+R^1$=ethylene) in the form of an oil with a boiling point 160°/0.1 mm; $n_D^{20}$ = 1.4930. IR-bands at 1,600 m, 1145 s, 900 s cm$^{-1}$.

The ratio of the trans isomer IVa-1 (4-methyl-8-methylene-4t,9-decadienal ethylene acetal) to the cis isomer IVb-1 (4-methyl-8-methylene-4c,9-decadienal ethylene acetal) amounts to ca 1:1. The isomer mixture may be separated by means of gas-chromatography.

The (4-ethylenedioxy-butyl)-triphenyl-phosphonium iodide (melting point 172°–177°) used in this example can be obtained as follows: 4-chlorobutyric acid chloride is reduced to 4-chlorobutanal according to Rosenmund, the aldehyde is acetalised with ethyleneglycol, the product obtained thereby is converted with sodium iodide into the ethylene acetal of 4-iodobutanal and the latter is reacted with triphenyl-phosphine.

EXAMPLE 3

146 mg (0.65 mmol) of the triene ethylene acetal of formula IV-1 (cis-trans isomer mixture) are dissolved in 3.7 ml of dioxan and 1.2 ml of 0.1-N sulphuric acid. The solution is boiled at reflux for 2 hours, the reaction product is taken up in ether, this solution washed until neutral with sodium bicarbonate solution and dried over sodium sulphate. After removal of the solvent, the oily residue is distilled. There are thus obtained 97 mg (83%) of a cis-trans isomer mixture of the triene aldehyde V-1,4-methyl-8-methylene-4,9-decadienal, of boiling point 100°/0.1 mm.

In an analogous manner, the pure cis and trans isomers IVb-1 and IVa-1 (obtained from the isomer mixture IV-1 by means of preparative gas chromatography) are saponified to the cis isomer Vb-1 (4-methyl-8-methylene-4c,9-decadienal) and to the trans isomer Va-1 (4-methyl-8-methylene-4t,9-decadienal) respectively. $n_D^{20}$ value and IR spectrum of the two isomers obtained are identical: $n_D^{20}$ = 1.4909; IR-bands at 2700 m, 1725 s, 1600 m, 900 s cm$^{-1}$.

EXAMPLE 4

175 mg (0.98 mmol) of the trans triene aldehyde Va-1 (4-methyl-8-methylene-4t,9-decadienal) and 318 mg (1.0 mmol) of the phosphorane VI, ($\alpha$-formylethylidene)-triphenyl-phosphorane, are dissolved in 5 ml of benzene. The solution is boiled at reflux for 40 hours, the benzene is thereupon removed by vacuum, the residue is treated with pentane, the phosphine oxide precipitates this way and is filtered off and the pentane is again evaporated from the filtrate. The residual oil is distilled. There are thus obtained 161 mg (75%) of gas-chromatographically pure trans $\beta$-sinensal VIIa-1 (2,6-dimethyl-10-methylene-2t,6t,11-dodecatrienal) of the approximate boiling point 100°/0.1 mm; $n_D^{20} = 1.0577$; IR-bands at 1700 s, 1600 w, 900 s cm$^{-1}$.

In a corresponding manner, there are obtained by reaction of 158 mg (0.89 mmol) of the cis triene aldehyde Vb-1 with 290 mg (0.91 mmol) of the phosphorane VI 157 mg (82%) of cis β-sinensal VIIb-1 of the approximate boiling point 100°/0.1 mm; $n_D^{20} = 1.5078$; IR-bands at 1700 s, 1600 w, 900 s cm$^{-1}$.

The phosphorane VI (melting point 220°–222°) can be obtained as follows: Ethyl iodide is reacted in benzene with triphenyl-phosphine to give ethyl-triphenyl-phosphonium iodide, and this is brought to reaction with butyl-lithium and formic acid methyl ester.

EXAMPLE 5

110 ml of ozone are led into a solution of 15 g (110 mmol) of myrcene in 150 ml of ethanol (or methanol) cooled to −80° in the course of about 4 hours. The solution is then briefly flushed with nitrogen, in order to expel excess ozone. A solution of 2.1 g (55.5 mmol) of sodium borohydride in 100 ml of methanol/water (1:1) is thereupon rapidly added dropwise at 0° and the mixture is then allowed to react at room temperature for 1–2 hours. The solution is thereupon concentrated to one-third of the volume at the rotary evaporator (bath-temperature 40°–50°), the residue taken up in ether, the ether solution thoroughly shaken twice with 1-molar acetic acid, washed neutral, dried over sodium sulphate and the ether evaporated off. After fractional distillation, there are obtained 5.8 g (48%) of gas-chromatographically pure 4-methylene-5-hexen-1-ol of boiling point 73°–75°/11 mm; $n_D^{20} = 1.4790$; IR-bands at 3350 s, 1605 m, 900 s cm$^{-1}$.

EXAMPLE 6

10 g (89 mmol) of 4-methylene-5-hexen-1-ol and 22 g (116 mmol) of tosyl chloride are dissolved in 50 ml of pyridine. The mixture is allowed to react at 50° for 1 hour. The reaction product is poured onto a mixture of ice and 80 ml of concentrated hydrochloric acid and the resulting mixture extracted with ether. The ether extracts are again thoroughly shaken once each with 1-N hydrochloric acid and with 1-N soda solution. After having been washed neutral with water, the ether solution is dried over sodium sulphate. After evaporation of the ether (bath-temperature 40°–50°, ca. 300 mg Hg), there remain approximately 12 g of a crude mixture of the corresponding diene tosylate and diene chloride (6-chloro-3-methylene-hexene). The chloride may be purified by distillation (boiling point 46°/1 mm; $n_D^{20} = 1.4771$), but the tosylate is thereby decomposed. For this reason, the tosylate-chloride mixture is converted as such into the iodide.

The tosylate-chloride mixture is dissolved in a suspension of 250 ml of acetone and 80 g (534 mmol) of sodium iodide and boiled at reflux temperature with stirring for 16 hours. Ca 200 ml of acetone are thereafter distilled off. The residue is taken up in water/ether. The ether extracts are thoroughly shaken, once with sodium thiosulphate solution and once with water. After having been dried over sodium sulphate, the ether is evaporated off. Fractional distillation yields 2 fractions:

1. Boiling point 50°–68°/11 mm; 4.1 g; $n_D^{20} = 1.4786$ (mainly chloride)
2. Boiling point 68°–76°/11 mm; 4.0 g; $n_D^{20} = 1.5321$ (iodide with trace of chloride)

6 g (27 mmol) of 6-iodo-3-methylene-1-hexene and 14 g (53 mmol) of triphenyl-phosphine are dissolved in 10 ml of benzene. The mixture is allowed to react at 60° for 24 hours. The (4-methylene-5-hexenyl)-triphenylphosphonium iodide which crystallizes out after this time is filtered off by suction, washed with benzene and dried. Yield 10.9 g (84%); melting point 146°.

The 6-Iodo-3-methylene-1hexene can also be obtained from 4-methylene-5-hexen-1-ol as follows:

2.02 g (4.5 mmol) of methyl-triphenyloxyphosphonium iodide are dissolved in 3 ml of absolute methylene chloride and treated at 0° with 0.5 g (4.5 mmol) 4-methylene-5-hexen-1-ol (dissolved in 0.6 ml of methylene chloride). After 10 minutes, the mixture is heated and then boiled at reflux temperature for 3 hours. There are thus obtained 333 mg of gas-chromatographically pure 6-iodo-3-methylene-1-hexene with $n_D^{20} = 1.5478$; IR-bands at 1600 m, 900 s cm$^{-1}$.

EXAMPLE 7

11.4 g (2.3 mmol) of (4-methylene-5-hexenyl)-triphenylphosphonium iodide are suspended in 80 ml of absolute tetrahydrofuran and 20 ml of absolute ether. 19.4 ml of 1.2- butyl-lithium solution (= 2.5 mmol of butyl-lithium) in hexane are added to the suspension at −20°. The solution thereby turns red. After 30 minutes the solution is cooled to −60° and treated with 4.5 g (2.6 mmol) of 4-oxo-pentanal diethyl acetal (IX: $R^1 = C_2H_5$), whereby the red solution decolourises. The mixture is subsequently stirred at room temperature for a further 3.5 hours, then poured onto ice-water and extracted with hexane. After drying over sodium sulphate, the hexane is evaporated off. The residual oil is chromatographed on the 10-fold amount of aluminum oxide. Through elution with benzene, there are obtained 2.6 g of thin layer chromatographically uniform material and therefrom, after distillation, 2.4 g (40%) of an oil boiling point 90°/0.1 mm. On the basis of a gas-chromatographic analysis, this product is a cis/-trans isomer mixture (2:1) of the triene acetal IV-1 ($R^1 = C_2H_5$). IR-bands at 1600 m, 900 s cm$^{-1}$.

EXAMPLE 8

2.0 g (8.0 mmol) of cis/trans trieneacetal IV-1 ($R^1=C_2H_5$) are dissolved in 25 ml of dioxan and 8 ml of 0.1-N sulphuric acid. The solution is allowed to stand at room temperature for 3 hours. It is neutralised by addition of solid sodium bicarbonate and the product is extracted with ether. After drying the ether extract over sodium sulphate, evaporation of the solvent and distillation of the residue, there are obtained 1.1 g (77%) of cis/trans triene aldehyde V-1 of boiling point 100°/0.1 mm; $n_D^{22} = 1.4831$; IR-bands at 1730 s, 1600 m, 900 s cm$^{-1}$.

EXAMPLE 9

4 g (8.3 mmol) of finely powdered and well dried (4-methylene-5-hexenyl)-triphenyl-phosphonium iodide are suspended in 24 ml of absolute tetrahydrofuran and 8 ml of absolute ether and treated at −20° with 6.8 ml of 1.2-M (8.2 mmol) butyl-lithium solution in hexane, whereby the characteristic red colouration rapidly apprears. After having reacted for 30 minutes at −20°, the solution is cooled to −70° and then treated with 1.52 g (8.3 mmol) of 6-oxo-2-methyl-2-heptenoic acid ethyl ester X-1 ($R^2=C_2H_5$). Very rapid decolourisation of the solution is thereby effected. The mixture is allowed to reach room temperature and stirred for a further 2.5 hours, then poured onto ice/water and extracted with ether. After drying over sodium sulphate, the solvent is evaporated off. There remain 3.7 g of a crude oil which, for the purpose of purification, is subjected to chromatography on the four-fold amount of silica gel (Merck 0.2-0.5). 1.3 g of the ester XI (thin layer-chromatographically pure) ($R^2=C_2H_5$), namely 2,6-dimethyl-10-methylene-2,6,11-dodecatrienoic acid ethyl ester, are eluted with benzene. By a distillation of this product there are obtained 895 mg (41%) of this ester with $n_D^{20} = 1.4938$. On the basis of gas-chromatographic analysis, this is an approximately 1:1 mixture of the 6-cis and the 6-trans isomers (2,6-dimethyl-10-methylene-2t,6c,11-dodecatrienoic acid ethyl ester and 2,6-dimethyl-10-methylene-2t,6t,11-dodecatrienoic acid ethyl ester).

IR-bands at 1705 s, 1650 w, 1600 w, 900 s cm$^{-1}$.

The cis/trans isomer mixture can be separated gas-chromatographically. Cis isomer: $n_D^{20} = 1.4942$; trans isomer: $n_D^{20} = 1.4946$.

EXAMPLE 10

33 mg (0.25 mmol) anhydrous aluminum chloride and 31 mg (0.78 mmol) of lithium aluminum hydride are suspended in 1 ml of absolute ether. To this suspension there are added at −80°, with the exclusion of moisture, 90 mg (0.34 mmol) of the cis/trans ester XI-1 obtained in accordance with Example 9 in a little ether. The reaction mixture is stirred at −30° for 15 minutes, subsequently again cooled to −80° and then treated with about 0.5 ml of methanol. The mixture is poured onto ice/0.1-N hydrochloric acid and extracted with ether. The ether solution is washed neutral with water and dried over sodium sulphate. The oil remaining after evaporation of the ether is distilled. There are thus obtained 58 mg (76%) of the colourless, gas-chromatographically pure cis/trans alcohol XII-1 (2,6-dimethyl-10-methylene-2t,6c/t,11-dodecatrienol). IR-bands at 3300 s, 1600 m, 900 s cm$^{-1}$. Boiling point approximately 100°/0.1 mm.

EXAMPLE 11

40 mg (0.18 mmol) of the cis/trans alcohol XII-1 obtained in accordance with Example 10 are added to a suspension of 140 mg of manganese dioxide in 1 ml of hexane. The mixture is stirred in a nitrogen atmosphere at room temperature for 21 hours, subsequently filtered and the filtrate freed from hexane. By distillation of the residue, there are obtained 19 mg (48%) of colourless, gas-chromatographically pure cis/trans aldehyde VII-1 (2,6-dimethyl-10-methylene-2t,6c/t,11-dodecatrienal) of boiling point approximately 100°/0.1 mm; IR-bands at 1695 s, 1650 m, 1600 m, 900 s cm$^{-1}$.

EXAMPLE 12

1 g (5.6 mmol) of trans triene aldehyde Va-1 (4-methyl-8-methylene-4t,9-decadienal) are added to a suspension, previously cooled to −20°, of 3.3 g (9.1 mmol) of (α-carbethoxyethylidene)-triphenyl phosphorane in 12 ml of absolute methylene chloride, whereupon the reaction mixture is allowed to stand for 30 hours at −20°. After removal of the solvent through vacuum, hexane is added, the precipitated phosphine oxide is filtered off and the filtrate is concentrated. The residue is distilled in a bulb tube. There are thus obtained 1.25 g (77%) of tetrane ester XI-1 (2,6-dimethyl-10-methylen-2t,6t, 11-dodecatrienoic acid ethyl ester) in the form of a colourles oil of b.p. 100°10,1 mm; IR-bands at 1720 s, 1650 w, 1600 w, 900 s cm$^{-1}$.

EXAMPLE 13

37 mmol of ozone are passed in the course of 80 minutes through a solution, previously cooled to −80°, of 5 g (37 mmol) of ocimene in 50 ml of methanol. The reaction mixture is thereafter briefly flushed with nitrogen. A solution of 700 mg (19 mmol) of sodium borohydride in 20 ml of methanol/water is then added dropwise at 0°. The mixture is allowed to react at room temperature for 2 hours. The mixture is then concentrated to ca one-third of the volume at the rotary evaporator (bath 35°–40°/20 mm Hg). The residue is taken up in ether, thoroughly shaken with 1-N acetic acid and then again washed neutral with sodium bicarbonate solution. After drying thee organic phase over sodium sulphate and evaporation of the ether, there remain 3.7 g of crude material which, after fractional distillation, yield 1.4 g (34%) of 4-methyl-3,5-hexadien-1-ol of boiling point 80°–81°/11 mm, $n_D^{20} = 1.4931$. IR-bands at 3300 s, 1650 w, 1610 w, 900 s cm$^{-1}$.

The cis/trans isomer mixture of 4-methyl-3,5-hexadien-1-ol may be resolved, e.g. by means of gas chromatography, into the pure cis and the pure trans isomer.

EXAMPLE 14

2.4 g (5.36 mmol) of triphenyl-phosphite-methoiodide are dissolved in 4.5 ml of methylene chloride and treated with 300 mg (2.68 mmol) of 4-methyl-3,5-hexadien-1-ol (cis/trans isomere mixture). The reaction mixture is refluxed for 15 minutes in a nitrogen atmosphere. It is subsequently diluted with ether, the ether layer washed three times with ice-cold 0.1N soda lye then twice with water and then dried over sodium sulfate. After removal of the solvent by vacuum an oil remains, which is purified by chromatography on 10 g of Silicagel (Merck 0.5-0.02). After elution of the column with hexane, there are obtained 480 mg (60%) of pure 6-iodo-3-methyl-1,3-hexadiene of b.p. 90°/11 mm; $n_D^{20} = 1.5656$; IR-bands at 1650 m, 1610 m, 900 s cm$^{-1}$.

In an analogous manner, the pure cis and trans iodide can be obtained starting from the corresponding pure cis or trans isomer respectively.

The 6-iodo-3-methyl-1,3-hexadiene obtained is converted in analogy to the method described in Example 6 with triphenyl phosphine to the (4-methyl-3,5-hexadienyl)-triphenyl phosphonium iodide. Thereby the phosphonium salt of a) the cis/trans isomer mixture of m.p. 113°–120°; b) the trans isomer of m.p. 126°–135°; c) the cis isomer of m.p. 102°–110°, are obtained with a yield of about 90%.

EXAMPLE 15

The phosphonium iodide obtained (4-methyl-3,5-hexadienyl)-triphenyl-phosphonium iodide) is condensed in a Wittig reaction with 4-oxo-pentanal diethyl acetal (IX:$R^1=C_2H_5$) to the corresponding triene acetal (4,8-dimethyl-4,7,9-decatrienal diethylacetal). The reaction is carried out in an analogous manner to the Wittig reaction described in Example 7. Starting from pure cis and from pure trans phosphonium iodide, there is obtained, respectively, an approximately 7:3 mixture of $\Delta^4$-cis/trans, $\Delta^7$-cis and of $\Delta^4$-cis/trans, $\Delta^7$-trans triene acetal. B.p. in the bulb tube about 100°/0.1 mm; TR-bands at 1650 m, 1600 m, 895 s cm$^{-1}$. The isomers may be resolved by gas chromatography.

EXAMPLE 16

The obtained triene acetal is saponified to the corresponding triene aldehyde (4,8-dimethyl-4,7,9-decatrienal) in analogy to the process of Example 8. B.p. in the bulb tube about 90°/0.1 mm; IR-bands at 270 m, 1740 s, 1650 m, 1600 m, 900 m cm$^{-1}$.

EXAMPLE 17

In analogy to the process described in Example 12, by a Wittig condensation of trans/trans triene aldehyde (4,8-dimethyl-4t,7t,9-decatrienal) with (α-carbethoxyethylidene)-triphenyl phosphoran (XIII: $R^2 = C_2H_5$) the corresponding all-trans tetraene ester (2,6,10-trimethyl-2t,6t,9t,11-dodecatetraenoic acid ethyl ester) is obtained. B.p. in the bulb tube about 100°/0.1 mm; IR-bands at 1715 s, 1650 w, 1610 w, 896 m cm$^{-1}$.

EXAMPLE 18

By reduction of the obtained all-trans tetraene ester (2,6,10-trimethyl-2t, 6t, 9t, 11-dodecatetraenoic acid ethyl ester) in analogy to the process described in Example 10, there is obtained the corresponding all-trans tetraene alcohol (2,6,10-trimethyl-2t, 6t, 9t, 11-dodecatetraenol). B.p. in the bulb tube about 100°–110°/0,1 mm; IR-bands at 3350 s, 1650 m, 1610 m, 995 m, 895 m cm$^{-1}$.

EXAMPLE 19

By oxidation of the obtained all-trans tetraene alcohol (2,6,10-trimethyl-2t, 6t, 9t, 11-dodecatrienol) in analogy to the process described in Example 11, there is obtained the corresponding all-trans tetraene aldehyde, α-sinensal (2,6,10-trimethyl-2t, 6t, 9t, 11-dodecatrienal). B.p. in the bulb tube about 100°/0.1 mm; IR-bands at 1725 w, 1650 m, 1610 m, 995 m, 895 m cm$^{-1}$.

EXAMPLE 20

1,6 g of 4-methylene-5-hexen-1-al (see Example 1) are dissolved, together with 5,5 g of silver nitrate, in 14 ml of ethyl alcohol and 7 ml of water. 49 ml of 1 n sodium hydroxide are added to the solution and the mixture is shaken for 20 hours at room temperature. The silver and the silver oxide are filtered off and the filtrate is extracted with pentane. 240 mg of the starting aldehyde are recovered. The aqueous phase is acidified with hydrochloric acid and extracted thrice with ether. The ether-extract is washed until neutral, dried and the solvent evaporated. Through a subsequent distillation in a bulb tube there are obtained 900 mg of a colorless oil; (50% of the theory); b.p. (bulb tube) of the 4-methylene-5-hexaenoic acid 90°/0,1 mm, $n_D^{24,5}$ 1,4752. IR-bands at 1715 s, 1600 m, 910 m.

Esterification of this product with diazomethane yields the corresponding methylester; b.p. (bulb tube) 85°/11 mm, $n_D^{24}$ 1,4605. IR bands at 3000 s, 1740 s, 1640 w, 1600 m, 1440 s, 900 s.

The foregoing illustrates the practice of this invention, which, however, is not to be limited thereby but is to be construed as broadly as permissible in view of the prior art and limited solely by the appended claims.

What is claimed is:
1. Process which comprises ozonizing a compound having the formula:

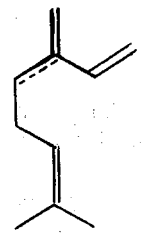

with not more than about 1 mole equivalent of ozone per mole of said compound at temperatures below ambient room temperature and decomposing the ozonization product in the presence of a reducing agent suitable for reducing ozonization products to alcohols, selected from the group consisting of a complex metal hydride, hydrogen catalytically activiated by noble-or transition metals or complexes of such said metals, to form the product having the formula:

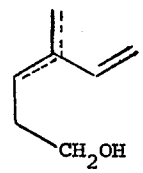 Ia

, converting the alcoholic hydroxyl group to an iodo substituent, reacting the resulting iodo-compound with triphenyl phosphine to give the corresponding phosphonium iodide, neutralizing said compound to form

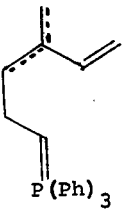

wherein Ph signifies a phenyl group,
reacting the latter with the ketone acetal of the formula

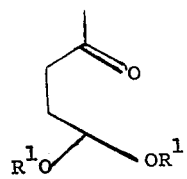

to form

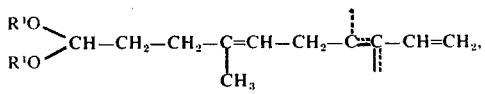

wherein R$^1$ signifies lower alkyl groups which may be linked together to form a lower alkylene group, hydrolyzing the resulting triene acetal which is obtained to the triene aldehyde of the formula:

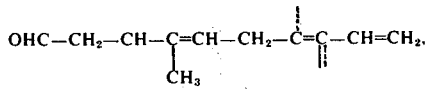

and reacting the resulting triene aldehyde with a phosphorane of the general formula:

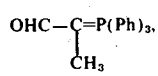

wherein Ph has the above significance, to give a corresponding tetraene aldehyde of the formula:

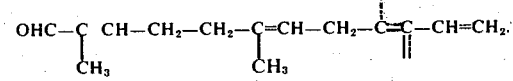

2. The process of claim 1, wherein myrcene is the starting material ozonized and the final product obtained has the formula

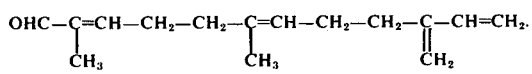

3. The process of claim 1, wherein ocimene is the starting material ozonized and the final product obtained has the formula

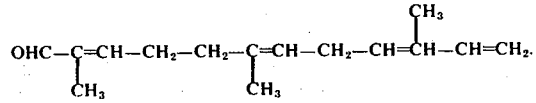

* * * * *